United States Patent [19]

Shaw

[11] Patent Number: 5,239,104

[45] Date of Patent: Aug. 24, 1993

[54] METHOD TO PREPARE ALKLYL XANTHATES OF PHENOLS

[75] Inventor: James E. Shaw, Bartlesville, Okla.

[73] Assignee: Phillips Petroleum Company, Bartlesville, Okla.

[21] Appl. No.: 644,763

[22] Filed: Jan. 23, 1991

[51] Int. Cl.⁵ .................. C07C 327/00; C07C 327/25; C07C 327/28
[52] U.S. Cl. .................................. 558/245; 558/247
[58] Field of Search ................................ 558/245, 247

[56] References Cited

U.S. PATENT DOCUMENTS

| | | | |
|---|---|---|---|
| 2,011,302 | 8/1935 | Rosenstein | 558/245 |
| 2,024,923 | 12/1935 | Hirschkind | 558/245 |
| 2,024,924 | 12/1935 | Hirschkind et al. | 558/247 X |
| 2,024,925 | 12/1935 | Hirschkind | 558/247 |

FOREIGN PATENT DOCUMENTS 0967584  5/1975  Canada .............................. 558/247

OTHER PUBLICATIONS

Chen, H. W., J. P. Fackler, D. P. Schussler and L. D. Thompson, 1978. J. Amer. Chem. Soc. 100(8): 2370–2375.

McKay, A. F., D. L. Garmaise, G. Y. Paris, S. Gelblum and R. J. Ranz, 1960. Can. J. Chem. 38P: 2042–2052.

S. R. Rao, *Xanthates and Related Compounds*, 1971 Marcel Dekker, Inc., New York.

Primary Examiner—Floyd D. Higel
Attorney, Agent, or Firm—Gary L. Haag

[57] ABSTRACT

Alkyl xanthates of phenols are prepared by a method comprising contacting an alkali metal salt of a phenol that is substantially free of water with carbon disulfide and an alkylating agent while employing a solvent in the reaction mixture.

15 Claims, No Drawings

METHOD TO PREPARE ALKLYL XANTHATES OF PHENOLS

FIELD OF THE INVENTION

This invention relates to the preparation of alkyl xanthates from phenols.

BACKGROUND OF THE INVENTION

Alkyl xanthates prepared from phenols are useful specialty chemicals. Primarily the alkyl xanthates are valuable as commodity chemicals. One of the desirable characteristics of the alkyl xanthates prepared from phenols is that the xanthates can be rearranged, then hydrolyzed to give thiophenols. The thiophenols can then be used in pharmaceuticals, herbicides, dyes, and as chemical intermediates.

Current methods for producing alkyl xanthates of phenols generally provide a poor yield of the xanthate product. One such method reacts carbon disulphide and potassium phenolate in dimethylformamide to form a potassium xanthate. Addition of methyl chloride to the reaction mixture converts the potassium xanthate to methyl xanthate (s-methyl phenyl xanthate), in a product yield of approximately 40%.

Because of a high demand for alkyl xanthates of phenols, alternative production methods are desirable. A method for producing the xanthates in a good yield as well as in an acceptable purity would be especially advantageous.

SUMMARY OF THE INVENTION

It is therefore an object of this invention to provide a method for producing alkyl xanthates of phenols.

It is a further object of this invention to provide a method for producing alkyl xanthates of phenols yielding a high percentage of product.

It is still a further object of this invention to provide a readily controllable method for producing alkyl xanthates of phenols.

It is yet another object of this invention to produce alkyl xanthates of phenols that have an acceptable purity level.

Other objects and aspects, as well as the advantages of this invention are apparent from a study of this disclosure and appended claims.

According to this invention, alkyl xanthates of phenols are prepared by a method comprising: (a) forming a reaction mixture by contacting a carbon disulfide with an alkali metal salt of a phenol, and (b) contacting said reaction mixture with an alkylating agent to form an alkyl xanthate product, wherein said alkali metal salt of a phenol contains substantially no water and a solvent is employed in the reaction mixture.

DETAILED DESCRIPTION OF THE INVENTION

In accordance with this invention, an alkyl xanthate of a phenol is formed by reacting an alkali metal salt of a phenol with a carbon disulfide and an alkylating agent. The procedure and selection of reagents utilized in this synthesis is a significant part of the invention. It has been discovered that if the alkali metal salt of the phenol contains substantially no water when the sulfur source is contacted with the salt of the phenol, the yield of the xanthate is increased. Further, it has also been discovered that the product yield is enhanced if a compatible solvent is employed during the synthesis. In the preferred embodiment of this invention, alkyl xanthates of phenols are prepared by the following synthesis:

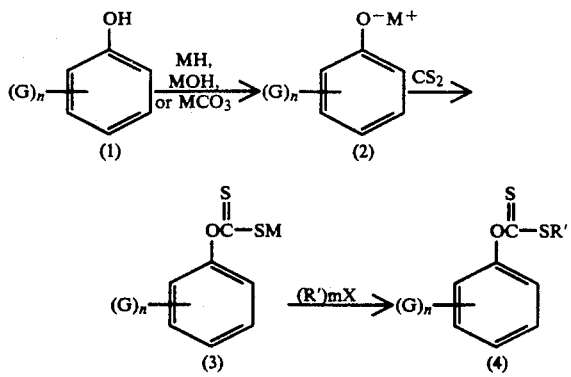

wherein structure (1) is a phenol and G can be H, Cl, Br, I, F, OH, $OCH_3$, $NO_2$, CN, R, or OR where R is an alkyl group with 1 to 20 carbons and n is an integer having a value of 0 to 3; structure (1) is reacted with a base that is selected from the group consisting of an alkali metal hydride (MH), alkali metal hydroxide (MOH), or an alkali metal carbonate ($MCO_3$) where M is an alkali metal selected from the group consisting of sodium, potassium, lithium, rubidium, or cesium; structure (2) is the alkali metal salt of the phenol; structure (3) is an intermediate product that is reacted with said $(R')_mX$ where R' is an alkyl group having 1 to 10 carbons, m is an integer having a value from 1 to 3, and X is selected from the group consisting of fluoride, chloride, bromide, iodide, or sulfate; and structure (4) is the final product, an alkyl xanthate of a phenol.

Generally the alkali metal salt of a phenol is formed by neutralizing a phenol with a base component. Once formed, the alkali metal salt of a phenol must be substantially free of water before the carbon disulfide is included in the reaction mixture. The absence of water in the reaction mixture before the carbon disulfide is employed can be accomplished by several techniques. These techniques include employing an alkali metal hydride as the base component or employing a water removal system after the phenol is reacted with the base.

When an alkali metal hydride is employed as a base component in this invention for the purpose of neutralizing the phenol, the resulting alkali metal salt of the phenol can be directly contacted with carbon disulfide. An intervening water removal step is not needed because the alkali metal salt of the phenol contains substantially no water upon formation.

Examples of such alkali metal hydrides that can be employed as the base component can be represented by the structure MH where M is an alkali metal as defined above. More preferably, the alkali metal hydride is sodium hydride, potassium hydride, or mixtures thereof, and most preferably, sodium hydride. At this time, alkali metal hydrides are somewhat expensive. Therefore, for purposes of economic efficiency, the alkali metal hydride bases are not a preferred technique employed for preparing a reaction mixture of an alkali metal salt of a phenol that contains substantially no water. Although employing an alkali metal hydride eliminates the need for a water removal system, the high cost of alkali metal hydrides currently discourages large scale operation of this technique.

Alternatively, a water removal system is necessary when a base with an hydroxide (—OH) or carbonate (—CO$_3$) anion is reacted with a phenol to form the alkali metal salt of the phenol. This water removal system is necessary because water is formed during the reaction between the phenol and the base. Bases with an —OH or —CO$_3$ anion are generally employed in this invention because of their availability and low cost. Preferably the base components with an —OH or a —CO$_3$ anion that can be employed in this invention include alkali metal hydroxides (MOH) and alkali metal carbonates (MCO$_3$). More preferably the base component is selected from the group consisting of sodium hydroxide, potassium hydroxide, lithium hydroxide, sodium carbonate, potassium carbonate, or mixtures thereof, although other alkali metals may be employed. At the present time, for purposes of availability and economy, the base component most preferably sodium hydroxide is employed.

The water removal system that can be used to remove water from the alkali metal salt of a phenol formed by reacting a —OH or —CO$_3$ anion base with a phenol is preferably a distillation system. Examples of distillation systems that are preferred include azeotropic distillation and nitrogen sparge distillation. More preferably an azeotropic distillation is employed.

In an azeotropic distillation system, water and another compound form an azeotrope and are distilled out together by employing either simple or fractional distillation. Compounds that form an azeotrope with water, and are therefore appropriate for use in this invention, include toluene, benzene, xylene, and other such aromatic compounds and mixtures thereof. Once the compound selected forms an azeotrope with the water. Both the compound and water are distilled off the reaction mixture at a low enough temperature so that no change occurs in the alkali metal salt of a phenol.

According to this invention, any phenol can be combined with the base component. Examples of phenols include those with one hydroxy (—OH) group on an aromatic ring system such as benzene, naphthalene, anthracene, phenanthrene, or those phenols with more than one hydroxy group on the aromatic ring such as resorcinol or hydroquinone. More preferably the phenol is selected from the following structures

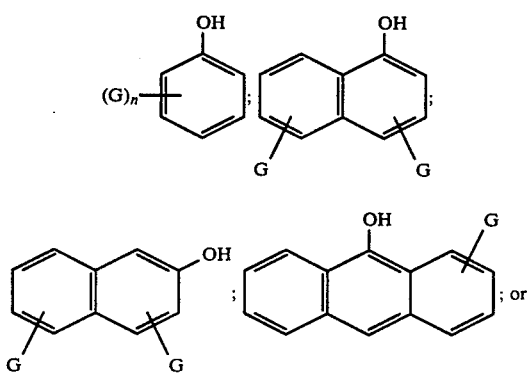

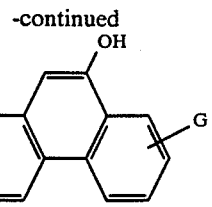

wherein G is a H, Cl, Br, I, F, OH, OCH$_3$, NO, CN, R, or OR where R is an alkyl group with 1 to 20 carbons and n is an integer having a value of 0 to 3. More preferably, the phenol is selected from the group consisting of phenol, o-cresol, m-cresol, p-cresol, o-chlorophenol, m-chlorophenol, p-chlorophenol, o-ethylphenol, p-ethylphenol, m-ethylphenol, 2,6-dimethylphenol, 3,5-dimethylphenol, and mixtures thereof. Currently a cresol is most preferred as the phenol neutralized by the base component.

The selection of a solvent compatible with the reagents employed in the alkyl xanthate synthesis is important in obtaining a good yield of the alkyl xanthate. The solvent may be included in the reaction mixture at any point, but preferably the solvent is employed at the onset of the inventive method and is included in the phenol and base reaction mixture. The primary function of the solvent is to keep the reagents in a homogenous solution and to ensure a complete reaction between reagents. Additionally, depending upon the selection of solvent, if distillation is employed to remove water, the solvent may keep the temperature of the reaction pot lower during distillation.

Preferred solvents include 2-methoxyethyl ether, sulfolane, 2-ethoxyethyl ether, dimethyl sulfoxide, diethylene glycol dibutyl ether, ethylene glycol diethyl ether, triethylene glycol dimethyl ether, and the like, and mixtures thereof. More preferably, the solvent is selected from the group consisting of sulfolane, dimethyl sulfoxide, 2-methoxyethyl ether, or mixtures thereof. Most preferably the solvent is a mixture of 2-methoxyethyl ether and sulfolane.

Carbon disulfide is contacted with the alkali metal salt of a phenol after the alkali metal salt of a phenol is substantially free of water. According to the invention, an alkylating agent is then contacted with the reaction mixture containing the alkali metal salt of a phenol and the carbon disulfide after said salt and carbon disulfide have substantially reacted. Preferably the alkylating agent is represented by the formula (R')$_m$X where R' is an alkyl group having from 1 to 3 carbon atoms, m is an integer from 1 to 3 and X is selected from the group consisting of fluoride, chloride, bromide, iodide, or sulfate. More preferably the alkylating agent is selected from the group consisting of methyl iodide, methyl chloride, methyl fluoride, methyl bromide, ethyl bromide, ethyl chloride, ethyl iodide, ethyl fluoride, dimethyl sulfate, diethyl sulfate, and mixtures thereof. For purposes of availability and cost at this time, methyl chloride is most preferably employed as the alkylating agent.

The amount of each reagent employed in the process is not critical. Generally, reagents are employed in equal amounts. Some excess base or carbon disulfide can be used. A large excess of alkyl halide can also be used.

The alkyl xanthate is formed upon contacting the alkylating agent with the reaction mixture. After completion of the final reaction, the alkyl xanthate is recovered. The work-up and recovery of the alkyl xanthate can be accomplished by appropriate methods known to those skilled in the art. For example, a solvent such as ethyl ether, methylene chloride, chloroform, tetrahydrofuran, cyclohexane, or mixtures thereof, is combined with the alkyl xanthate reaction mixture to form a solution. The solution is then washed with water, followed by a drying step with, for example, anhydrous magnesium sulfate, whereupon the xanthate is separated by the solvent by an evaporation technique.

The main impurities found in the final product are generally the solvent and distillation azeoptropic compound, if employed, and unreacted reagents or intermediate products. Purity of the final alkyl xanthate product can be improved by recovering the final product by distillation under reduced pressure.

The examples following should be taken as exemplary and not exclusive in illustrating the invention.

EXAMPLE I

In a 1 L, 3 necked flask equipped with a $N_2$ inlet, magnetic stirring bar, pressure equalizing funnel, and Dean Stark trap with condenser and drying tube, 54.0 g of p-cresol and 250 ml sulfolane were charged. The flask was then flushed with $N_2$ for the first 5 minutes then turned down to a slow flow (approximately 1 bubble every 2 seconds). The flask was thereafter placed in a room temperature water bath with 20.0 g sodium hydroxide (NaOH) pellets being added by funnel. The mixture was stirred to dissolve the NaOH pellets with slight heating for 15 minutes.

After the NaOH was dissolved, 150 ml of toluene were added. Heat was then applied to reflux to azeotrope water out of the flask. Approximately 10 ml of water was removed, then 146 ml of toluene was refluxed off. The reaction flask was subsequently cooled to room temperature and the flask was returned to the room temperature water bath where 31.5 ml of carbon disulfide were added through a dropping funnel over a period of 30 minutes. The flask was stirred for an additional 2.5 hours whereupon 34.2 ml of methyl iodide ($CH_3I$) was added over a period of 30 minutes with a dropping funnel to the flask, while the flask was set in the water bath again.

The mixture was then stirred overnight and worked-up by using 500 ml $H_2O$ and 300 ml ethyl ether to transfer mixture to a 2 L funnel, where the 2 L funnel was agitated and the ether layer separated and saved. The water layer was separated and extracted with 150 ml of ethyl ether. This extract was then combined with the first ether extract and washed three times with 50 ml $H_2O$ each time, dried with anhydrous magnesium sulfate, rotovaped, weighed, and analyzed using a gas chromatograph. The recovered product, methyl xanthate of p-cresol, weighed 95.7 g and had a purity of 62.3%. The calculated yield of product was 60.2%.

In this Example, as in Examples II-VII, the main impurities in the final product were the solvent, toluene, and unreacted p-cresol or methylated p-cresol. A purer xanthate product could be obtained by distillation under reduced pressure.

EXAMPLE II

The procedure of Example I was employed except that 250 ml of 2-methoxyl ethyl ether was substituted for sulfolane. When 34.2 ml of methyl iodide was added over a 30 minute period, the solution turned solid. To get the solid back into solution, 300 ml of sulfolane was added. The resulting solution was then stirred overnight. The mixture was then worked-up using the procedure of Example I. The product, methyl xanthate of p-cresol, weighed 115.5 g and had a 64.5% purity. The calculated yield of product was 75.3%.

EXAMPLE III

The procedure of Example I was employed with the following difference: a combination of sulfolane and 2-methoxyethyl ether was used as the solvent. The amount of solvent employed was 100 ml sulfolane and 150 ml of 2-methoxyethyl ether. The resulting methyl xanthate of p-cresol weighed 123.6 g and had a 66.2% purity. The calculated yield of product was 82.6%.

EXAMPLE IV

The procedure of Example I was employed except that o-cresol was used as a reagent instead of p-cresol and the solvent system was 100 ml of sulfolane and 150 ml of 2-methoxyethyl ether. The weight of the product, methyl xanthate of o-cresol, was 122.5 g and had a 66.1% purity. The calculated yield of product was 81.8%.

EXAMPLE V

The procedure of Example I was followed with exception that the solvent system employed differed as well as the selection of alkylating agent. Just prior to the distillation, 250 ml of dimethyl sulfoxide was employed for purposes of acting as a solvent. After the azeotropic distillation step, the entire solution turned solid after returning to room temperature. To convert the mixture back to a solution, 250 ml of sulfolane was added. Once the reaction mixture was back into solution, and the carbon disulfide was added and stirred, 41.0 ml (0.55 mole) of ethyl bromide ($CH_3CH_2Br$) was employed as the alkylating agent.

The weight of the product, ethyl xanthate of p-cresol, was 97.2 g and had a 51.4% purity. The calculated yield of product was 47.1%.

EXAMPLE VI

The procedure of Example I was employed except that methyl chloride ($CH_3Cl$) was used as the alkylating agent rather than $CH_3I$, and the solvent system was 100 ml of sulfolane and 150 ml of 2-methoxyethyl ether. The product, methyl xanthate of a p-cresol, weighed 138.1 g and had a purity of 50.9%. The calculated yield of product was 71%.

EXAMPLE VII

The procedure of Example I was employed with the exception that methyl iodide was replaced by ethyl bromide (41.0 ml) and the solvent system was 100 ml of sulfolane and 150 ml of 2-methoxyethyl ether. The product, ethyl xanthate of a p-cresol, had a weight 136.2 g and a 54.1% purity. The calculated yield of product was 69.5%.

That which is claimed is:

1. A method of preparing alkyl xanthates comprising:
   (a) forming a reaction mixture by contacting a carbon disulfide with an alkali metal salt of a phenol;
   (b) contacting said reaction mixture with an alkylating agent to form an alkyl xanthate; and
   (c) recovering said alkyl xanthate, wherein said alkali metal salt of a phenol contains substantially no water and a solvent selected from the group consisting of 2-methoxyethyl ether, sulfolane, 2-ethoxyethyl ether, dimethyl sulfoxide, diethyleneglycol dibutyl ether, triethyleneglycol dimethyl ether, or mixtures thereof is employed in said reaction mixture.

2. A method according to claim 1 wherein
(a) said alkali metal salt of a phenol is formed by reacting a base selected from the group consisting of alkali metal hydroxides, alkali metal carbonates, or mixtures thereof, with a phenol selected from the group consisting of

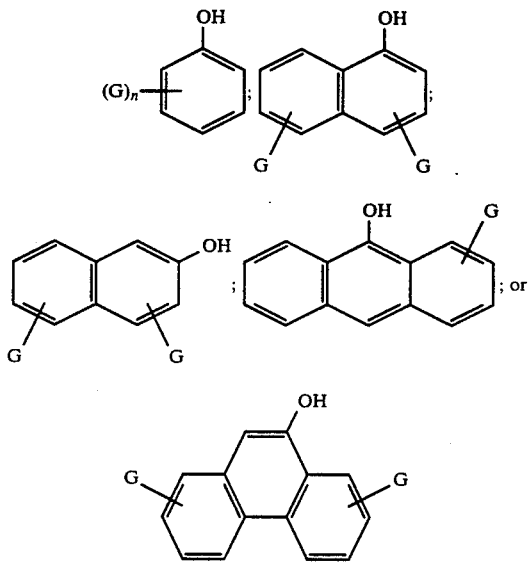

or mixtures thereof, wherein G is selected from the group consisting of H, Cl, Br, I, F, OH, $OCH_3$, $NO_2$, CN, R, or OR where R is an alkyl group with 1 to 20 carbons and n is an integer having a value of 0 to 3;
(b) said alkylating agent is selected from the group consisting of $(R')_m$ wherein R' is an alkyl group having from 1 to 3 carbon atoms, m is an interger from 1 to 3, and x is selected from the group consisting of fluoride, chloride, bromide, iodide, or sulfate;
wherein water is substantially removed from said alkali metal salt of a phenol by distillation.

3. A method according to claim 2 wherein
(a) said base is selected from the group consisting of sodium hydroxide, potassium hydroxide, lithium hydroxide, sodium carbonate, potassium carbonate, or mixtures thereof and said phenol is selected from the group consisting of phenol, o-cresol, m-cresol, p-cresol, o-chlorophenol, m-chlorophenol, p-chlorophenol, o-ethylphenol, p-ethylphenol, m-ethylphenol, 2,6-dimethylphenol, 3,5-dimethylphenol, or mixtures thereof;
(b) said alkylating agent is selected from the group consisting of methyl iodide, methyl chloride, methyl fluoride, methyl bromide, ethyl bromide, ethyl chloride, ethyl iodide, ethyl fluoride, dimethyl sulfate, diethyl sulfate, and mixtures thereof; and said distillation is an azeotropic distillation where an azeotrope is formed with water by employing a compound selected from the group consisting of toluene, benzene, or xylene; and said solvent is selected from the group consisting of sulfolane, dimethyl sulfoxide, 2-methoxyethyl ether, or mixtures thereof.

4. A method according to claim 3 wherein said base is sodium hydroxide; said phenol is a cresol, said solvent is a mixture of sulfolane and 2-methoxyethyl ether; and said azeotropic distillation compound is toluene.

5. A method according to claim 4 wherein
(a) said phenol is p-cresol; and
(b) said alkylating agent is methyl iodide.

6. A method according to claim 4 wherein
(a) said phenol is o-cresol; and
(b) said alkylating agent is methyl iodide.

7. A method according to claim 4 wherein
(a) said phenol is o-cresol; and
(b) said alkylating agent methyl chloride.

8. A method according to claim 4 wherein
(a) said phenol is p-cresol; and
(b) said alkylating agent is methyl chloride.

9. A method according to claim 4 wherein
(a) said phenol is p-cresol; and
(b) said alkylating agent is ethyl bromide.

10. A method according to claim 4 wherein
(a) said phenol is o-cresol; and
(b) said alkylating agent is ethyl bromide.

11. A method according to claim 1 wherein
(a) said alkali metal salt of a phenol is formed by reacting a base selected from the group consisting of alkali metal hydrides and mixtures thereof with a phenol selected from the group consisting of phenol, o-cresol, p-cresol, m-cresol, o-chlorophenol, m-chlorophenol, p-chlorophenol, o-ethylphenol, p-ethylphenol, m-ethylphenol, 2,6-dimethylphenol, 3,5-dimethylphenol, or mixtures thereof;
(b) said alkylating agent is selected from the group consisting of methyl iodide, methyl chloride, methyl fluoride, methyl bromide, ethyl iodide, ethyl chloride, ethyl fluoride, ethyl bromide, dimethyl sulfate, diethyl sulfate, or mixtures thereof.

12. A method according to claim 11 wherein
(a) said base is selected from the group consisting of potassium hydride, sodium hydride, or mixtures thereof; and said phenol is selected from the group consisting of o-cresol, p-cresol, or mixtures thereof;
(b) said alkylating agent is selected from the group consisting of methyl iodide, methyl chloride, or ethyl bromide; and said solvent is selected from the group consisting of sulfolane, dimethyl sulfoxide, 2-methoxyethyl ether, or mixtures thereof.

13. A method according to claim 12 wherein said solvent is a mixture of sulfolane and 2-methoxyethyl ether.

14. A method according to claim 13 wherein
(a) said base is sodium hydride and said phenol is o-cresol; and
(b) said alkylating agent is methyl chloride.

15. A method for preparing alkyl xanthate of phenol comprising:
(a) contacting sodium hydroxide and cresol in sulfolane solvent to form a reaction mixture containing alkali metal salt of phenol and water;
(b) adding toluene to said mixture of step (a) to form a toluene-bearing mixture;
(c) removing water from said mixture of step (b) by azeotropic distillation thereby forming a substantially water-free alkali metal salt of phenol-bearing mixture;

(d) contacting said mixture of step (c) and carbon disulfide to form a xanthate salt-bearing mixture; and (e) contacting said mixture of step (d) and an alkylating agent selected from the group consisting of methyl iodide, methyl chloride, methyl fluoride, methyl bromide, ethyl iodide, ethyl chloride, ethyl fluoride, ethyl bromide, dimethyl sulfate, diethyl sulfate, or mixtures thereof to form an alkyl xanthate of phenol-bearing solution.

* * * * *